(12) United States Patent
Inoue et al.

(10) Patent No.: US 10,495,896 B2
(45) Date of Patent: Dec. 3, 2019

(54) OPTICAL MODULE AND OBSERVATION DEVICE

(71) Applicant: HAMAMATSU PHOTONICS K.K., Hamamatsu-shi, Shizuoka (JP)

(72) Inventors: Takashi Inoue, Hamamatsu (JP); Hirotoshi Terada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/782,005

(22) PCT Filed: Mar. 25, 2014

(86) PCT No.: PCT/JP2014/058289
§ 371 (c)(1),
(2) Date: Oct. 2, 2015

(87) PCT Pub. No.: WO2014/162926
PCT Pub. Date: Oct. 9, 2014

(65) Prior Publication Data
US 2016/0054576 A1   Feb. 25, 2016

(30) Foreign Application Priority Data
Apr. 5, 2013 (JP) .................... 2013-079805

(51) Int. Cl.
*G02B 27/28* (2006.01)
*G01N 21/64* (2006.01)
(Continued)

(52) U.S. Cl.
CPC ....... *G02B 27/283* (2013.01); *G01N 21/6458* (2013.01); *G02B 5/3016* (2013.01);
(Continued)

(58) Field of Classification Search
CPC .............. G02B 27/283; G02B 27/0025; G02B 27/0905; G02B 5/3016; G02B 21/0032;
(Continued)

(56) References Cited

U.S. PATENT DOCUMENTS 5,552,840 A   9/1996 Ishii et al.
5,701,201 A   12/1997 Okazaki
(Continued)

FOREIGN PATENT DOCUMENTS

CA   2 336 553   1/2007
CN   1441279   9/2003
(Continued)

OTHER PUBLICATIONS

P. Prieto et al., "Adaptive optics with a programmable phase modulator: applications in the human eye." Optical Society of America (OSA), Optics Express, vol. 12, No. 17, Aug. 23, 2004, pp. 4059-4071.
(Continued)

*Primary Examiner* — Angela K Davison
(74) *Attorney, Agent, or Firm* — Drinker Biddle & Reath LLP

(57) ABSTRACT

An optical module (1A) includes a polarization beam splitter (10A) having a light splitting surface (11), polarization elements (20, 40), and respectively arranged on an optical path of a first polarization component (L2) transmitted through the light splitting surface (11) and an optical path of a second polarization component (L4) reflected by the light splitting surface (11), a reflective SLM (30) that modulates and reflects the first polarization component (L2) passing through the polarization element (20), and a reflective SLM (50) that modulates and reflects the second polarization component (L4) passing through the polarization element (40). The first modulation light (L3) passing through the
(Continued)

polarization element (20) again and then reflected by the light splitting surface (11) and the second modulation light (L5) passing through the polarization element (40) again and then transmitted through the light splitting surface (11) are combined with each other.

5 Claims, 8 Drawing Sheets

(51) Int. Cl.
  *G02B 21/00* (2006.01)
  *G02B 5/30* (2006.01)
  *G02B 27/00* (2006.01)
  *G02B 27/09* (2006.01)
(52) U.S. Cl.
  CPC ..... *G02B 21/0032* (2013.01); *G02B 21/0092* (2013.01); *G02B 27/0025* (2013.01); *G02B 27/0905* (2013.01); *G01N 2201/0675* (2013.01); *G02B 21/0076* (2013.01)
(58) Field of Classification Search
  CPC ............ G02B 21/0092; G02B 21/0076; G02B 21/002; G02B 21/0024; G02B 21/0068; G02B 21/082; G02B 21/084; G02B 21/086; G01N 21/6458; G01N 2201/0675; G02F 2001/133541; G02F 1/025; G02F 2203/24; G02F 2203/50; H01L 43/02; H01L 43/10
  USPC ..................................... 349/193, 194, 5, 8, 9
  See application file for complete search history.

(56) References Cited

U.S. PATENT DOCUMENTS

| | | | |
|---|---|---|---|
| 6,625,181 B1 | 9/2003 | Oshemkov et al. | |
| 6,742,897 B1 | 6/2004 | Tajiri | |
| 6,924,893 B2* | 8/2005 | Oldenbourg | G02B 21/0004 356/369 |
| 7,148,936 B1* | 12/2006 | Hirota | G02B 27/1026 349/9 |
| 7,990,611 B2* | 8/2011 | Betzig | G01N 21/6445 359/370 |
| 8,957,349 B2 | 2/2015 | Matsumoto et al. | |
| 9,152,034 B2 | 10/2015 | Yamaguchi | |
| 2003/0230710 A1 | 12/2003 | Wolleschensky et al. | |
| 2006/0256261 A1* | 11/2006 | Chiang | G02F 1/133528 349/98 |
| 2012/0147280 A1* | 6/2012 | Osterman | G02B 27/26 349/9 |
| 2012/0162609 A1* | 6/2012 | Yamaguchi | G02B 27/26 353/20 |

FOREIGN PATENT DOCUMENTS

| | | |
|---|---|---|
| CN | 101191990 | 6/2008 |
| CN | 101606097 | 12/2009 |
| CN | 102385151 | 3/2012 |
| EP | 2 109 793 | 10/2009 |
| JP | S64-079722 | 3/1989 |
| JP | 2000-019455 A | 1/2000 |
| JP | 2001-091842 A | 4/2001 |
| JP | 2004-102225 A | 4/2004 |
| JP | 2005-144524 A | 6/2005 |
| JP | 2008-276043 A | 11/2008 |
| JP | 2010-518431 A | 5/2010 |
| JP | 4877963 | 2/2012 |
| JP | 5090783 | 12/2012 |
| WO | WO 01/037029 | 5/2001 |
| WO | WO 2008/010532 | 1/2008 |
| WO | WO 2008/095609 | 8/2008 |
| WO | WO 2008095609 * | 8/2008 ............ G02B 26/06 |
| WO | WO-2008/105312 A1 | 9/2008 |

OTHER PUBLICATIONS

X. Zeng et al., "Parallel lensless optical correlator based on two phase-only spatial light modulators," Optical Society of America (OSA), Optics Express, vol. 19, No. 13, Jun. 20, 2011, pp. 12594-12604.

Chen Liu, "Engineering Optics", National Defense Industry Press, Aug. 31, 2012, p. 292-293 with attached English-language translation.

Mingyou Zhang, "Optically Controlled Phased Array Radar", National Defense Industry Press, Apr. 30, 2008, p. 83-84 with attached English-language translation.

Dingguo Sha, "Optical Testing Testing", Beijing Institute of Technology Press, Oct. 31, 2010, p. 138-139 with attached English-language translation.

* cited by examiner

OPTICAL MODULE AND OBSERVATION DEVICE

TECHNICAL FIELD

The present invention relates to an optical module and an observation apparatus.

BACKGROUND ART

Non-Patent Literature 1 discloses aberration correction performed using a PPM (Programmable Phase Modulator) that is a spatial light modulator in a fundus measuring device.

CITATION LIST

Non-Patent Literature

Non-Patent Literature 1: Pedro Prieto, Enrique Fernandez, Silvestre Manzanera, and PabloArtal, "Adaptive optics with programmable phase modulator: applications in the human eye," Optics Express, Volume 12, Issue 17, pp. 4059-4071 (2004)

SUMMARY OF INVENTION

Technical Problem

In recent years, a technology for modulating an intensity distribution or a phase distribution of observation light using an SLM for correction of lens aberrations in an observation apparatus or the like has been studied. However, only a linear polarization component may be modulated according to a configuration of the SLM. For example, in a configuration described in Non-Patent Literature 1, only linear polarization light that can be modulated in the PPM is extracted from light (observation light) from a fundus input to the PPM by a linear polarizer. Thus, when the SLM can modulate only the linear polarization component, other polarization components are not used and light use efficiency (an intensity ratio between the observation light and the light after modulation) is suppressed to be small.

The present invention has been made in view of such problems, and an object thereof is to provide an optical module capable of increasing light use efficiency in a device that modulates input light, such as observation light, and the observation apparatus including the optical module.

Solution to Problem

In order to solve the above problems, a first optical module according to the present invention includes a polarization beam splitter including a light splitting surface for reflecting an s-polarization component included in input light and transmitting a p-polarization component; a first polarization element having nonreciprocal optical activity to rotate a polarization plane, and arranged on an optical path of a first polarization component transmitted through the light splitting surface in the input light; a first reflective SLM for modulating the first polarization component passing through the first polarization element to generate first modulation light, and reflecting the first modulation light to the first polarization element; a second polarization element having nonreciprocal optical activity to rotate a polarization plane, and arranged on an optical path of a second polarization component reflected by the light splitting surface in the input light; and a second reflective SLM for modulate the second polarization component passing through the second polarization element to generate second modulation light, and reflecting the second modulation light to the second polarization element, wherein the first modulation light passing through the first polarization element again and then reflected by the light splitting surface and the second modulation light passing through the second polarization element again and then transmitted through the light splitting surface are combined with each other and output from the polarization beam splitter.

In the first optical module, the polarization plane of the first polarization component (p-polarization component) transmitted through the polarization beam splitter is rotated by the first polarization element, and then the first polarization component is input to the first reflective SLM. The first polarization component is modulated by the first reflective SLM to be the first modulation light, and the polarization plane of the first modulation light is rotated by the first polarization element again. Since the first polarization element has nonreciprocal optical activity, the first modulation light reciprocating through the first polarization element in this way can include the s-polarization component reflected by the polarization beam splitter. Further, preferably, the polarization plane of the first polarization component before modulation may be rotated 45° by the first polarization element, and the polarization plane of the first modulation light after modulation may be further rotated 45° by the first polarization element.

Further, the polarization plane of the second polarization component (s-polarization component) reflected by the polarization beam splitter is rotated by the second polarization element, and then the second polarization component is input to the second reflective SLM. The second polarization component is modulated by the second reflective SLM to be the second modulation light, and the polarization plane of the second modulation light is rotated again by the second polarization element. Since the second polarization element has nonreciprocal optical activity, the second modulation light reciprocating through the second polarization element in this way may include a p-polarization component transmitted through the polarization beam splitter. Further, preferably, the polarization plane of the second polarization component before modulation may be rotated 45° by the second polarization element, and the polarization plane of the second modulation light after modulation may be further rotated 45° by the second polarization element.

Then, the first modulation light including the s-polarization component is reflected by the polarization beam splitter, and the second modulation light including the p-polarization component is transmitted through the polarization beam splitter. These modulation lights are combined with each other and output from the polarization beam splitter.

As described above, in the first optical module, the p-polarization component and the s-polarization component of the input light (for example, observation light) can be separated and then modulated, and the first and second modulation lights after modulation can be combined and output. Therefore, according to the first optical module, it is possible to effectively use both the p-polarization component and the s-polarization component of the input light and increase light use efficiency.

Further, in the first optical module, the first and second reflective spatial light modulators may be liquid crystal types, and an alignment direction of liquid crystal of the first reflective SLM and an alignment direction of liquid crystal of the second reflective SLM are orthogonal to each other.

Thus, it is possible to efficiently modulate the first and second polarization components having orthogonal polarization planes in the first and second reflective SLMs, respectively.

Further, the first optical module may further include: a polarization element having reciprocal optical activity and arranged on an optical path between the polarization beam splitter and the first reflective SLM or on an optical path between the polarization beam splitter and the second reflective SLM. Thus, an angle of the polarization plane of the first polarization component immediately before the first polarization component is input to the first reflective SLM, or an angle of the polarization plane of the second polarization component immediately before the second polarization component is input to the second reflective SLM can be arbitrarily controlled.

Further, a first observation apparatus according to the present invention includes any one of the first optical modules; a gathering optical system for gathering observation light from an observation target and causing the observation light to be input as the input light to the optical module; an image-forming optical system for forming an image of light output from the optical module; and a photodetector for detecting the light of which the image has been formed by the image-forming optical system. According to the first observation apparatus, by including the first optical module described above, it is possible to increase light use efficiency of the observation light.

Further, in the first observation apparatus, a pinhole may be arranged on an optical path between the image-forming optical system and the photodetector. Accordingly, it is possible to reduce noise light included in the light of which the image has been formed by the image-forming optical system and to enable clearer observation.

A second optical module according to the present invention includes: a first polarization beam splitter including a light splitting surface for reflecting an s-polarization component included in input light and transmits a p-polarization component; a first polarization element having nonreciprocal optical activity to rotate a polarization plane, and arranged on an optical path of a first polarization component in the input light reflected by the light splitting surface of the first polarization beam splitter; a first reflective SLM for modulating the first observation light passing through the first polarization element to generate first modulation light and reflecting the first modulation light to the first polarization element; a second polarization beam splitter including a light splitting surface for reflecting the s-polarization component and transmitting the p-polarization component, and for receiving a second polarization component in the input light transmitted through the light splitting surface of the first polarization beam splitter using the light splitting surface; a second polarization element having nonreciprocal optical activity to rotate a polarization plane, and arranged on an optical path of the second polarization component subjected to one of transmission and reflection by the light splitting surface of the second polarization beam splitter; and a second reflective SLM for modulating the second polarization component passing through the second polarization element to generate second modulation light, and reflecting the second modulation light to the second polarization element, wherein the first modulation light passes through the first polarization element again, is transmitted through the light splitting surface of the first polarization beam splitter, and then is output, and the second modulation light passes through the second polarization element again, and is output through the other of the transmission and the reflection by the light splitting surface of the second polarization beam splitter.

The polarization plane of the first polarization component transmitted through the first polarization beam splitter is rotated by the first polarization element, and then the first polarization component is input to the first reflective SLM. The first observation light is modulated by the first reflective SLM to be the first modulation light, and the polarization plane of the first modulation light is rotated by the first polarization element again. Since the first polarization element has nonreciprocal optical activity, the first modulation light reciprocating through the first polarization element in this way can include the s-polarization component reflected by the polarization beam splitter, and is output to the outside of the optical module after the reflection. Further, preferably, the polarization plane of the first observation light before modulation may be rotated 45° by the first polarization element, and the polarization plane of the first modulation light after modulation may be further rotated 45° by the first polarization element.

Further, the second polarization component reflected by the first polarization beam splitter is input to the second polarization beam splitter. The second polarization component is subjected to one of the transmission and the reflection by the second polarization beam splitter, and the polarization plane thereof is rotated by the second polarization element and then is input to the second reflective SLM. The second polarization component is modulated by the second reflective SLM to be the second modulation light, and the polarization plane of the second modulation light is rotated again by the second polarization element. Since the second polarization element has the nonreciprocal optical activity, the second modulation light reciprocating through the second polarization element in this way is subjected to the other of the transmission and the reflection by the second polarization beam splitter, and output to the outside of the second optical module. Further, preferably, the polarization plane of the second polarization component before modulation may be rotated 45° by the second polarization element, and the polarization plane of the second modulation light after modulation may be further rotated 45° by the second polarization element.

As described above, the second optical module can separate, modulate, and output the p-polarization component and the s-polarization component of the input light. Therefore, according to the second optical module, it is possible to effectively use both the p-polarization component and the s-polarization component of the input light, and to increase light use efficiency.

Further, the second optical module may further include an optical path length adjustment element provided on an optical path between the first polarization beam splitter and the first reflective SLM.

Further, the second optical module may further include a polarization element having reciprocal optical activity and provided on an optical path between the first polarization beam splitter and the second reflective SLM. Accordingly, the polarization plane of the second modulation light reflected by the light splitting surface of the second polarization beam splitter can be rotated, and the second modulation light can preferably be transmitted through the light splitting surface of the first polarization beam splitter.

Further, a second observation apparatus according to the present invention includes any one of the second optical modules; a gathering optical system for gathering observation light from an observation target and causing the observation light to be input as the input light to the optical module; an image-forming optical system for forming an image of light output from the optical module; and a photodetector for detecting the light of which the image has been formed by the image-forming optical system. According to the second observation apparatus, by including the second optical module described above, it is possible to increase light use efficiency of the observation light.

Further, in the second observation apparatus, a pinhole may be arranged on an optical path between the image-forming optical system and the photodetector. Accordingly, it is possible to reduce noise light included in the light of which the image has been formed by the image-forming optical system and to enable clearer observation.

Advantageous Effects of Invention

According to the optical module and the observation apparatus according to the present invention, it is possible to increase light use efficiency in a device that modulates input light, such as observation light.

DESCRIPTION OF EMBODIMENTS

Hereinafter, embodiments of the optical module and the observation apparatus according to the present invention will be described in detail with reference to the accompanying drawings. Further, in the description of the drawings, the same elements are denoted with the same reference signs, and repeated description will be omitted.

First Embodiment

Figure 1:
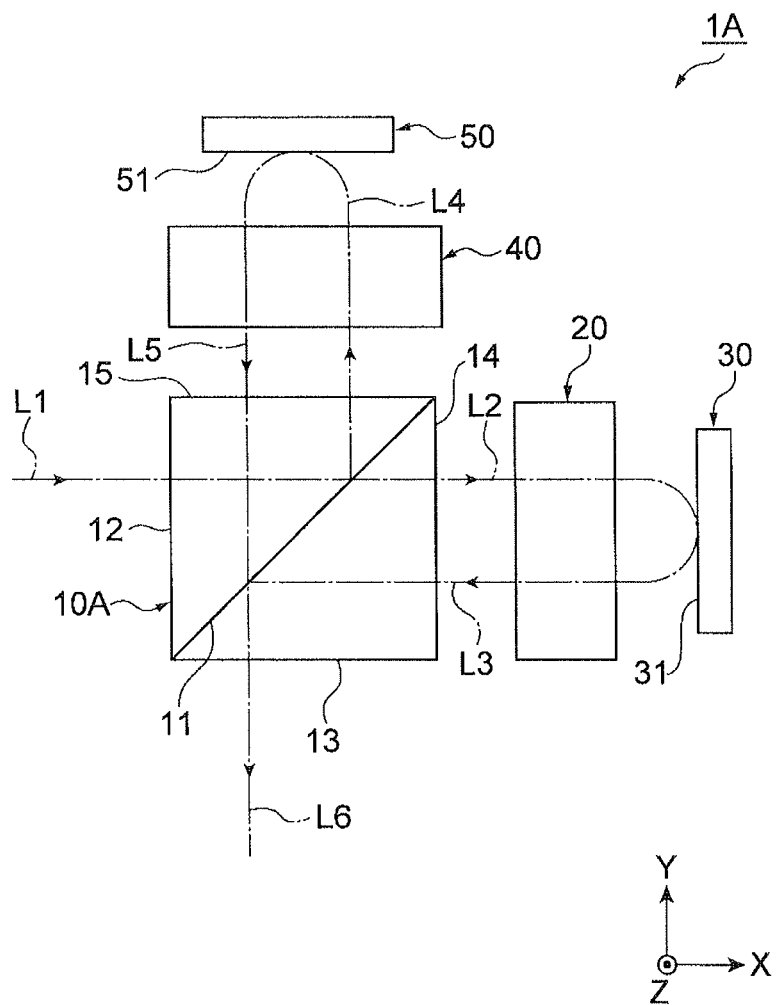
FIG. 1 is a diagram illustrating a configuration of an optical module according to a first embodiment of the present invention.
Figure 2:
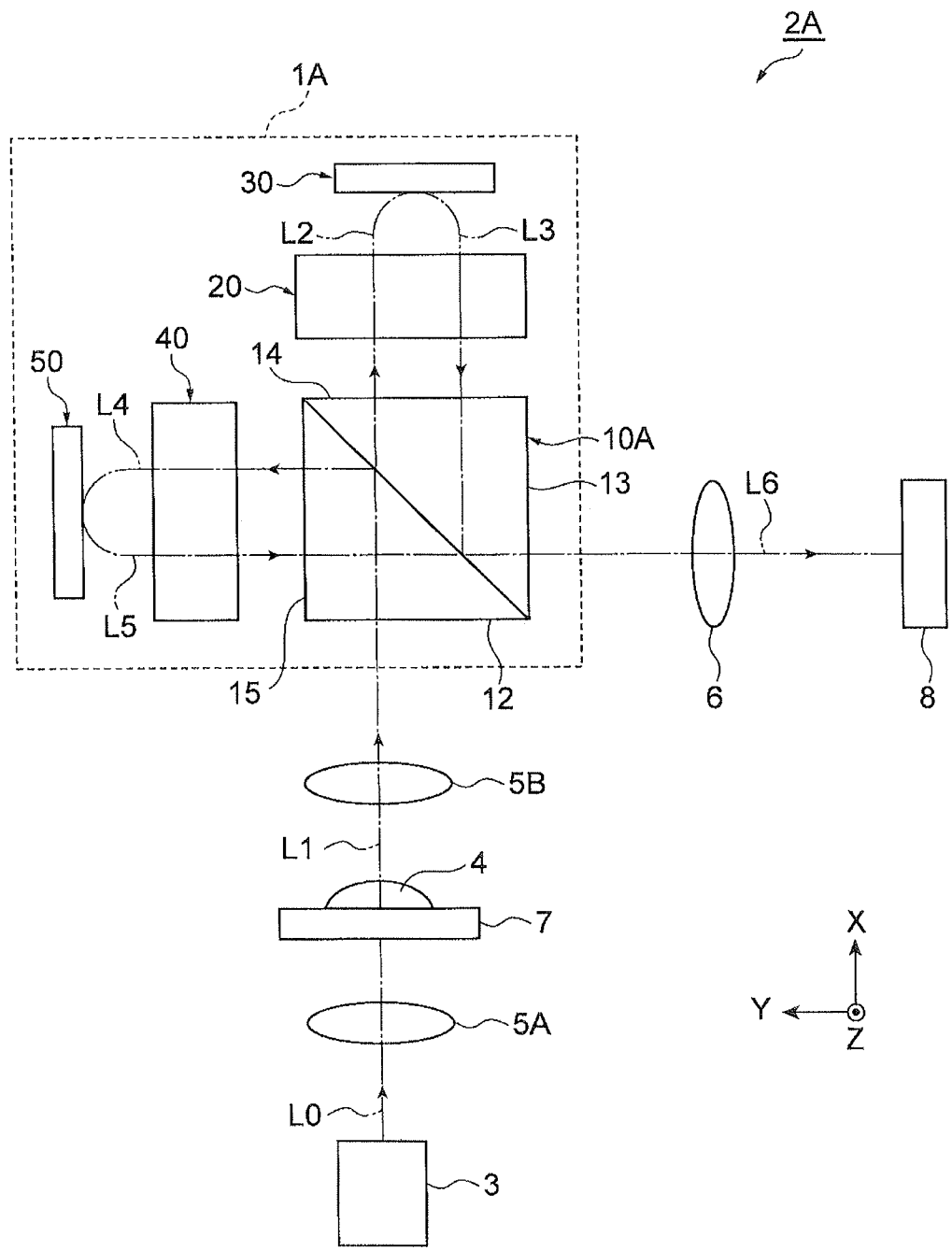
FIG. 2 is a diagram illustrating a configuration of an observation apparatus including the optical module of the first embodiment.

FIG. 1 is a diagram illustrating a configuration of an optical module 1A according to a first embodiment of the present invention. Further, FIG. 2 is a diagram illustrating a configuration of an observation apparatus 2A including the optical module 1A. Further, for ease of understanding, an XYZ orthogonal coordinate system is shown together in FIGS. 1 and 2. Further, in FIGS. 1 and 2, for ease of understanding, an optical axis of light L2 and an optical axis of light L3 are separate, but in fact, the optical axis of the light L2 and the optical axis of the light L3 partially overlap. The same applies to light L4 and light L5.

As illustrated in FIG. 1, the optical module 1A includes a polarization beam splitter 10A, a first polarization element 20, a first reflective SLM 30, a second polarization element 40, and a second reflective SLM 50.

The polarization beam splitter 10A is an optical part having a light splitting surface 11. The light splitting surface 11 is inclined with respect to both of a first direction (an X-axis direction in this embodiment) and a second direction (a Y-axis direction in this embodiment) intersecting the first direction, and its inclination angle is, for example, 45°. The light splitting surface 11 reflects an s-polarization component included in light input from these directions, and transmits a p-polarization component. The light splitting surface 11 receives observation light L1 which is input from the outside of the optical module 1A along the X-axis direction. This observation light L1 is light including both of the p-polarization component and the s-polarization component, and is, for example, light of non-polarization (random polarization), circular polarization, elliptical polarization, or linear polarization that is neither the p-polarization nor the s-polarization, or light in which light of the s-polarization having a different wavelength from the light of the p-polarization overlaps the light of the p-polarization.

Further, a cross-sectional shape of the polarization beam splitter 10A along an XY plane is a rectangular shape. Also, the polarization beam splitter 10A includes a light input surface 12, a light output surface 13, a first surface 14, and a second surface 15 appearing in this cross section. The light input surface 12 is along a plane intersecting the X-axis direction, and receives the observation light L1. The light output surface 13 is along a plane intersecting the Y-axis direction, and outputs combined modulation light L6. The first surface 14 is along the plane intersecting the X-axis direction, and the light input surface 12 and the first surface 14 are arranged side by side in the X-axis direction. The second surface 15 is along a plane intersecting the Y-axis direction, and the light output surface 13 and the second surface 15 are arranged side by side in the Y-axis direction. Among the four surfaces, the light input surface 12 and the second surface 15 are arranged on one surface side of the light splitting surface 11, and the light output surface 13 and the first surface 14 are arranged on the other surface side of the light splitting surface 11.

The first polarization element 20 is optically coupled to the first surface 14 of the polarization beam splitter 10A, and is arranged on an optical path of a first polarization component L2 transmitted through the light splitting surface 11 in the observation light L1 (a p-polarization component at a time at which the observation light L1 is transmitted through the light splitting surface 11). Further, the optical path of the first polarization component L2 refers to an optical path of the light transmitted through the light splitting surface 11 in the observation light L1. The first polarization element 20 of this embodiment is arranged beside the light splitting surface 11 of the polarization beam splitter 10A in the X-axis direction. The first polarization element 20 has nonreciprocal optical activity for rotating the polarization plane of the first polarization component L2. Here, the nonreciprocal optical activity is a polarization characteristic that causes a direction of rotation. 1.5 of light propagating in a forward direction and a direction of rotation of light propagating in an opposite direction to be the same as each other. For example, when the polarization plane of the light passing through the first polarization element 20 from any direction is rotated a predetermined angle (for example, 45° or 135°) in a predetermined direction, the polarization plane of light passing through the first polarization element 20 from an opposite direction is further rotated the same angle in the above predetermined direction. For example, when the predetermined angle is 45° and light reciprocates through the first polarization element 20, the polarization plane of the light is rotated 90°. The first polarization element 20 preferably includes a Faraday rotator in one example.

Further, while a ½-wavelength plate including an optical crystal also rotates the polarization plane of the passing light, the rotation direction of light propagating in the forward direction and the rotation direction of the light propagating in the opposite direction are opposite to each other in the ½-wavelength plate, and thus, when the light reciprocates, the polarization plane of the light returns to an original state. Therefore, the ½-wavelength plate is not a polarization element having nonreciprocal optical activity, and is not used as the first polarization element 20.

The first reflective SLM 30 modulates the first polarization component L2 passing through the first polarization element 20 to generate first modulation light L3, and reflects the first modulation light L3 to the first polarization element 20. Various SLMs such as a phase modulation SLM, an intensity modulation (amplitude modulation) SLM, or a polarization modulation SLM are applied as the first reflective SLM 30. The first reflective SLM 30 has a modulation surface 31 including a plurality of one-dimensionally or two-dimensionally arranged areas (pixels). The first reflective SLM 30 modulates the phase, the strength or the like of the first polarization component L2 in each of the plurality of areas to generate the first modulation light L3. In one example, the first reflective SLM 30 is an LCOS (Liquid Crystal on Silicon) SLM having parallel-aligned nematic liquid crystal. The first reflective SLM 30 is not limited to an electrically addressed liquid crystal element and may be, for example, an optically addressed liquid crystal element, an element having an electro-optical effect material other than liquid crystal, an element including a number of micro mirrors, or a deformable mirror type optical modulator.

The second polarization element 40 is optically coupled to the second surface 15 of the polarization beam splitter 10A, and is arranged on the optical path of the second polarization component L4 reflected by the light splitting surface 11 in the observation light L1 (the s-polarization component at a time at which the observation light L1 is reflected by the light splitting surface 11). Further, the optical path of the second polarization component L4 refers to an optical path of light reflected by the light splitting surface 11 in the observation light L1. The second polarization element 40 of this embodiment is arranged beside the light splitting surface 11 of the polarization beam splitter 10A in the Y-axis direction. The second polarization element 40 has nonreciprocal optical activity for rotating the polarization plane of the second polarization component L4. Further, the definition of the nonreciprocal optical activity is the same as that in the first polarization element 20 described above. The second polarization element 40 preferably includes a Faraday rotator in one example.

The second reflective SLM 50 modulates the second polarization component L4 that has passed through the second polarization element 40 to generate second modulation light L5, and reflects the second modulation light L5 to the second polarization element 40. Various SLMs such as a phase modulation SLM, an intensity modulation (amplitude modulation) SLM, or a polarization modulation SLM are applied as the second reflective SLM 50, similarly to the first reflective SLM 30. The second reflective SLM 50 has a modulation surface 51 including a plurality of one-dimensionally or two-dimensionally arranged areas (pixels). The second reflective SLM 50 modulates a phase, strength or the like of the second polarization component L4 in each of the plurality of areas to generate the second modulation light L5. In one example, the second reflective SLM 50 is an LCOS type SLM having parallel-aligned nematic liquid crystal. The second reflective SLM 50 is not limited to an electrically addressed liquid crystal element and may be, for example, an optically addressed liquid crystal element, an element having an electro-optical effect material other than liquid crystal, an element including a number of micro mirrors, or a deformable mirror type optical modulator.

Further, when the reflective SLMs 30 and 50 are LCOS type SLMs, only a linear polarization component of which a vibration direction is parallel to an alignment direction of the liquid crystal is modulated, and thus the reflective SLMs 30 and 50 may be arranged according to the angle of the polarization plane after the rotation by the polarization elements 20 and 40.

As illustrated in FIG. 2, the observation apparatus 2A of this embodiment includes a light source 3, an illumination optical system 5A, a gathering optical system 5B, an image-forming optical system 6, a stage 7, and a photodetector 8, in addition to the above-described optical module 1A.

The light source 3 is a light source that outputs illumination light L0 (for example, non-polarization light) including a p-polarization component and an s-polarization component. The light source 3 is optically coupled to an observation target (measurement target) 4 placed on the stage 7 through the illumination optical system 5A including, for example, a lens. Further, the gathering optical system 5B is arranged on an optical path between the observation target 4 and a light input surface 12 of the polarization beam splitter 10A, and guides the observation light L1 generated by the illumination light L0 being transmitted through the observation target 4 to the polarization beam splitter 10A. The gathering optical system 5B includes, for example, an objective lens. The image-forming optical system 6 forms an image of combined modulation light L6 output from the optical module 1A toward the photodetector 8. The photodetector 8 is a device that converts an input optical image into electrical image data, and is optically coupled to a light output surface 13 of the polarization beam splitter 10A via the image-forming optical system 6.

Operations of the optical module 1A and the observation apparatus 2A having the above configuration will be described. When illumination light L10 is output from the light source 3, the illumination light L10 is transmitted through the observation target 4. In this case, an optical image of the observation target 4 is generated as the observation light L1. The observation light L1 passes through a gathering optical system 5B and reaches the polarization beam splitter 10A. In the observation light L1 input to the light input surface 12 of the polarization beam splitter 10A in the X-axis direction, the first polarization component L2 is transmitted through the light splitting surface 11 and is output from the first surface 14. Further, the second polarization component L4 is reflected by the light splitting surface 11 and output from the second surface 15. The first polarization component L2 passes through the first polarization element 20, but in this case, the polarization plane of the first polarization component L2 is rotated, for example, 45° or 135° in a predetermined direction from a p-polarization plane by the first polarization element 20. Then, the first polarization component L2 is modulated by the first reflective SLM 30 to be the first modulation light L3, and is simultaneously reflected to the first polarization element 20. The first modulation light L3 passes through the first polarization element 20 again, but in this case, the polarization plane of the first modulation light L3 is rotated, for example, 45° or 135° in the above predetermined direction by the first polarization element 20. As a result, the first modulation light L3 mainly includes the s-polarization component (or consists of only the s-polarization component).

On the other hand, the second polarization component L4 passes through the second polarization element 40, but in this case, the polarization plane of the second polarization component L4 is rotated, for example, 45° or 135° in a predetermined direction from the s-polarization plane by the second polarization element 40. Then, the second polarization component L4 is modulated by the second reflective SLM 50 to be the second modulation light L5 and simultaneously reflected to the second polarization element 40. The second modulation light L5 passes through the second polarization element 40 again, but in this case, the polarization plane of the second modulation light L5 is rotated, for example, 45° or 135° in the above predetermined direction by the second polarization element 40. As a result, the second modulation light L5 mainly includes the p-polarization component (or consists of only the p-polarization component).

Then, the first modulation light L3 including the s-polarization component is reflected by the polarization beam splitter 10A, and the second modulation light L5 including the p-polarization component is transmitted through the polarization beam splitter 10A. These modulation lights L3 and L5 are combined with each other and output from the light output surface 13 of the polarization beam splitter 10A as combined modulation light L6. An image is formed from the combined modulation light L6 by the image-forming optical system 6 and imaged by the photodetector 8.

Effects obtained by the optical module 1A and the observation apparatus 2A of this embodiment described above will be described. In the optical module 1A, the p-polarization component (first polarization component L2) and the s-polarization component (second polarization component L4) of the observation light L1 can be separated and then modulated, and the first and second modulation lights L3 and L5 after modulation can be combined and output. Therefore, according to the optical module 1A of the present embodiment, it is possible to effectively use both of the p-polarization component and the s-polarization component of the observation light L1 and increase light use efficiency (a ratio of intensity of the observation light L1 and intensity of an optical image input to the photodetector 8). Accordingly, it is possible to observe the observation light L1 with a larger amount of light than in a conventional case, and to clearly observe the observation target 4 even when light intensity of the observation light L1 is very small.

Further, according to the optical module 1A and the observation apparatus 2A of the present embodiment, different modulation patterns can be applied to the first and second modulation lights L3 and L5. Accordingly, for example, two modulation patterns having a different optical phase distribution or light intensity distribution within a plane perpendicular to the optical axis can be applied. Alternatively, it is possible to correct the aberrations independently for each polarization component. Thus, according to the optical module 1A and the observation apparatus 2A of the present embodiment, it is possible to provide a user with a variety of observation forms, as compared to a conventional device. Further, since the first and second modulation lights L3 and L5 that have been individually modulated are combined and output, it is possible to reduce speckles included in the optical image input to the photodetector 8. In the present embodiment, the first reflective SLM 30 and the second reflective SLM 50 may present the same modulation pattern.

Further, in the optical module 1A, the two reflective SLMs 30 and 50 are arranged around one polarization beam splitter 10A. Also, the light (first polarization component L2) input to the first reflective SLM 30 is input from the polarization beam splitter 10A, and the light after modulation (first modulation light L3) is reflected to the polarization beam splitter 10A. Similarly, light (second polarization component L4) input to the second reflective SLM 50 is input from the polarization beam splitter 10A, and the light after the modulation (second modulation light L5) is reflected to the polarization beam splitter 10A. With this configuration, the light can be input and reflected in normal directions of the respective modulation surfaces 31 and 51 of the reflective SLMs 30 and 50, and thus it is easy to adjust the optical axis and it is possible to increase efficiency of input to the SLM and efficiency of output from the SLM. Further, the optical axis of the observation light L1 and the optical axis of the combined modulation light L6 can be caused to be orthogonal rather than oblique, and thus it is possible to facilitate a connection to the gathering optical system 5B or the image-forming optical system 6 and to reduce generation of aberrations. Further, since the light is caused to reciprocate in a part of the optical path, it is possible to simplify and miniaturize the configuration of the entire optical system.

In the optical module 1A of this embodiment, when the first and second reflective SLMs 30 and 50 are liquid crystal types, only a linear polarization component of which a vibration direction is parallel to the alignment direction of the liquid crystal is modulated as described above. Therefore, it is preferable that the first and second reflective SLMs 30 and 50 be arranged such that the alignment direction of the liquid crystal of the first reflective SLM 30 is orthogonal to the alignment direction of the liquid crystal of the second reflective SLM 50. Thus, the first and second polarization components L2 and L4 of which the polarization planes are orthogonal to each other can be efficiently modulated in the first and second reflective SLMs 30 and 50, respectively.

First Modification Example

Figure 3:
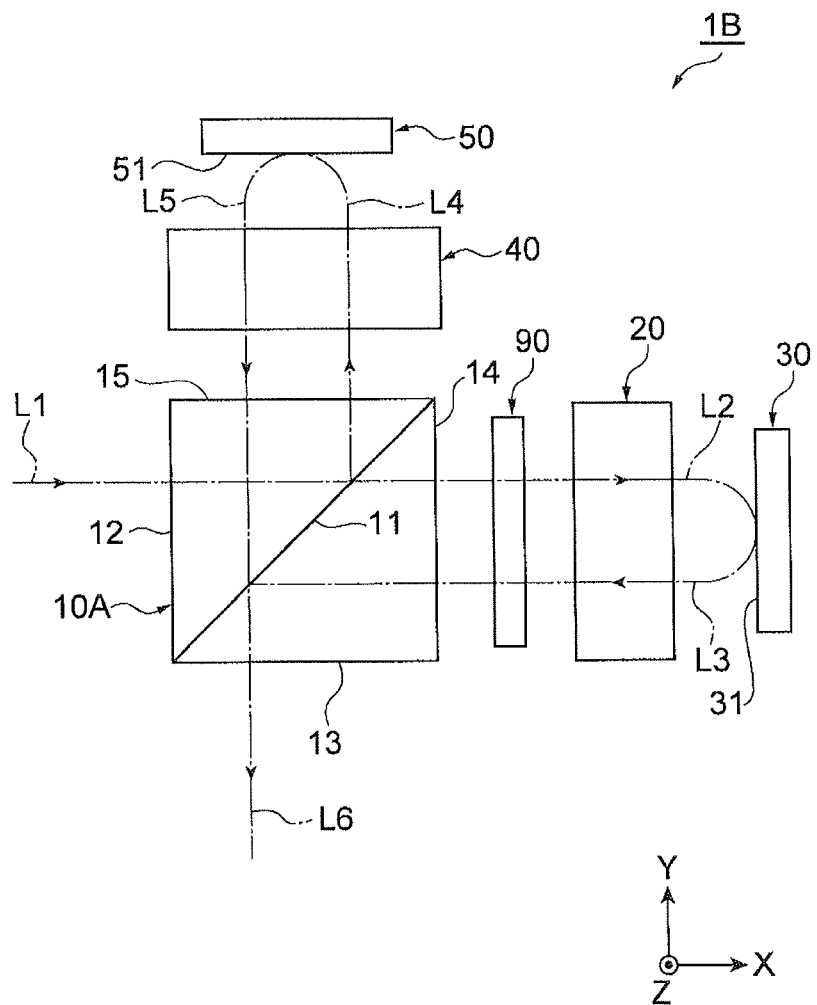
FIG. 3 is a diagram illustrating a configuration of an optical module according to a first modification example of the first embodiment.

FIG. 3 is a diagram illustrating a configuration of an optical module 1B according to a modification example of the above embodiment. The optical module 1B of this modification example further includes a ½-wavelength plate 90 that is a polarization element having reciprocal optical activity, in addition to the configuration of the optical module 1A of the above embodiment. In this modification example, the ½-wavelength plate 90 is arranged on an optical path between the polarization beam splitter 10A and the first reflective SLM 30. An example in which the ½-wavelength plate 90 is arranged on an optical path between the polarization beam splitter 10A and the first polarization element 20 is illustrated in FIG. 3. A delay axis of the ½-wavelength plate 90 is set to, for example, 45° with respect to the polarization plane of the first polarization component L2 that passes through the ½-wavelength plate 90.

In this example, the first polarization component L2 transmitted through the light splitting surface 11 of the polarization beam splitter 10A passes through the ½-wavelength plate 90. In this case, the polarization plane of the first polarization component L2 is rotated 90° in a certain rotation direction from a p-polarization plane by the ½-wavelength plate 90. Then, the first polarization component L2 reciprocates between the first polarization element 20 and the first reflective SLM 30 to be the first modulation light L3, and passes through the ½-wavelength plate 90 again. In this case, the polarization plane of the first modulation light L3 is rotated 90° in a direction opposite to the above direction by the ½-wavelength plate 90. As a result, the polarization plane of the first modulation light L3 when the first modulation light L3 is input to the polarization beam splitter 10A is the same as that in the first embodiment.

In this modification example, the polarization plane of the first polarization component L2 when the first polarization component L2 is input to the first reflective SLM 30 is rotated by the polarization element having reciprocal optical activity. Accordingly, the angle of the polarization plane of the first polarization component L2 immediately before the first polarization component L2 is input to the first reflective SLM 30 can be arbitrarily controlled. Thus, for example, when the first and second reflective SLMs 30 and 50 are liquid crystal SLMs, a light distribution direction of liquid crystal of the first reflective SLM 30 can be arbitrarily set. Accordingly, for example, the light distribution direction of the liquid crystal of the first reflective SLM 30 and the light distribution direction of the liquid crystal of the second reflective SLM 50 can be aligned (parallelized to each other), and control of the first and second reflective SLMs 30 and 50 can be common to modulation data input to the first and second reflective SLMs 30 and 50.

Further, the ½-wavelength plate 90 may be arranged on the optical path between the first polarization element 20 and the first reflective SLM 30 or may be arranged on the optical path between the polarization beam splitter 10A and the second reflective SLM 50 (between the polarization beam splitter 10A and the second polarization element 40 or between the second polarization element 40 and the second reflective SLM 50). When the ½-wavelength plate 90 is arranged on the optical path between the polarization beam splitter 10A and the second reflective SLM 50, an angle of the polarization plane of the second polarization component L4 immediately before the second polarization component L4 is input to the second reflective SLM 50 can be arbitrarily controlled, and it is possible to achieve the same effects described above.

Second Embodiment

Figure 4:
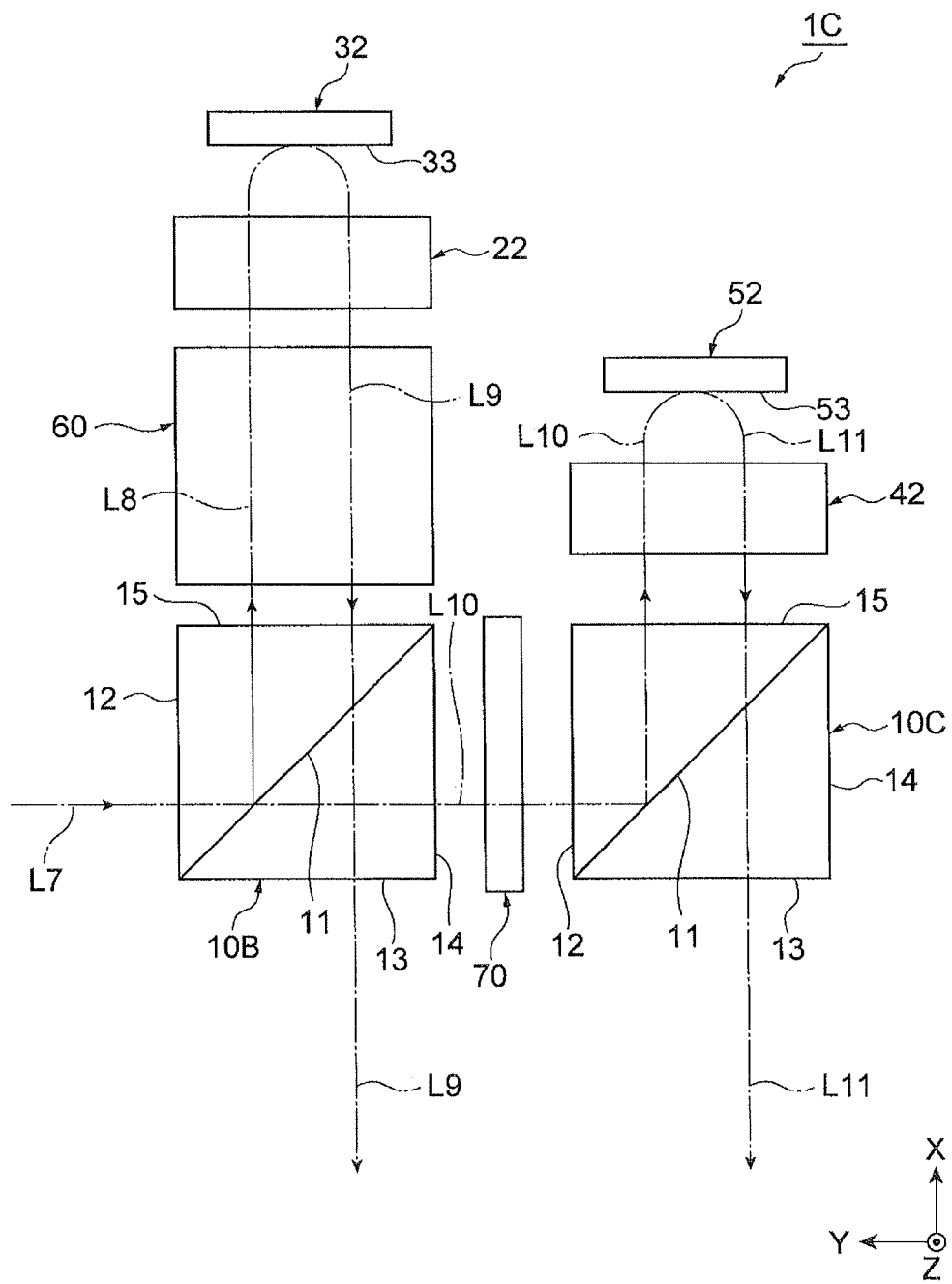
FIG. 4 is a diagram illustrating a configuration of an optical module according to a second embodiment of the present invention.
Figure 5:
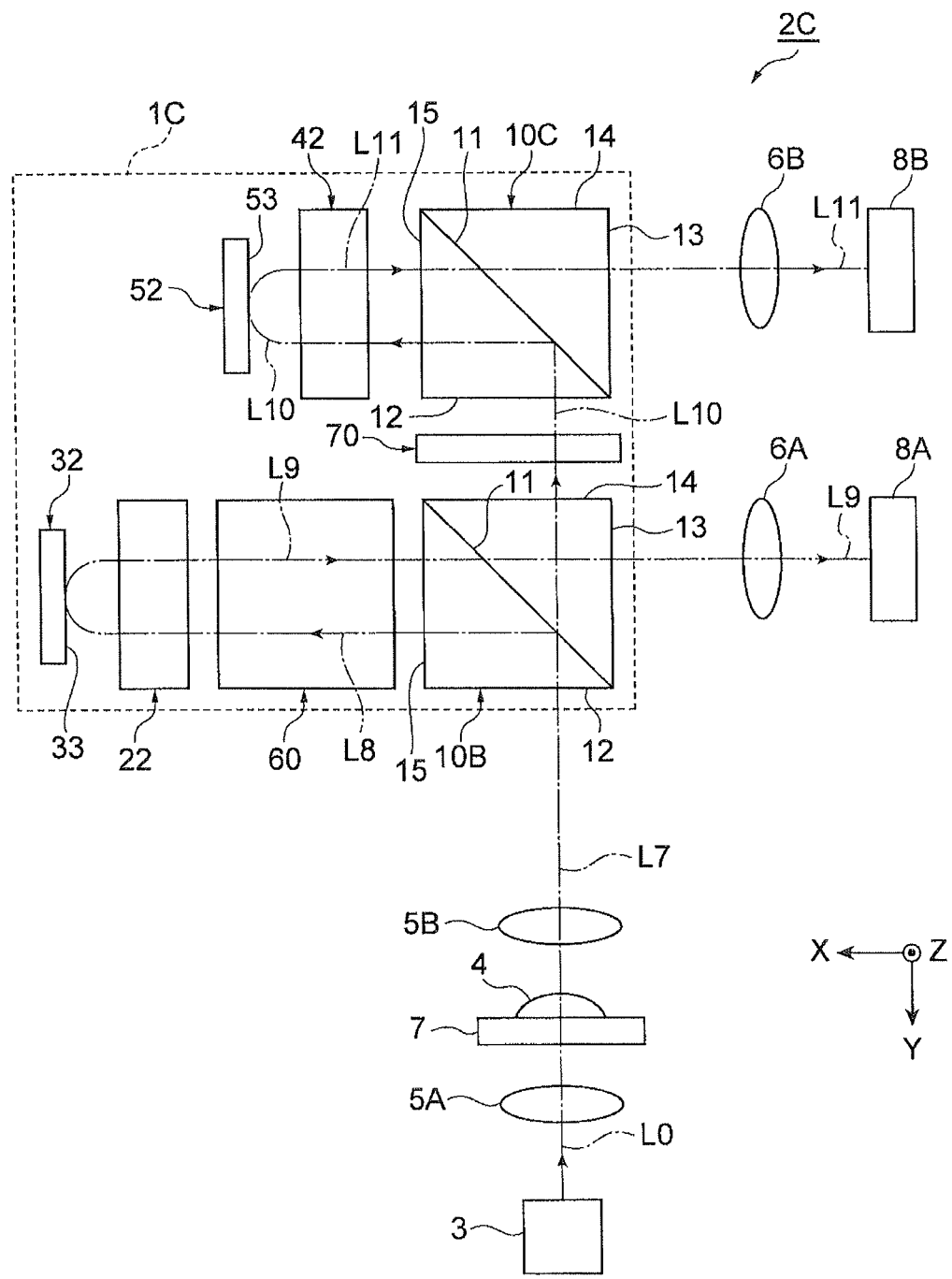
FIG. 5 is a diagram illustrating a configuration of an observation apparatus including the optical module of the second embodiment.

FIG. 4 is a diagram illustrating a configuration of an optical module 1C according to a second embodiment of the present invention. Further, FIG. 5 is a diagram illustrating a configuration of an observation apparatus 2C including the optical module 1C. Further, for ease of understanding, an XYZ orthogonal coordinate system is also illustrated in FIGS. 4 and 5. Further, in FIGS. 4 and 5, for ease of understanding, optical axes of light L8 and light L9 are separate, but in fact, the optical axis of the light L8 and the optical axis of the light L9 partially overlap. The same applies to light L10 and light L11.

As illustrated in FIG. 4, the optical module 1C includes a first polarization beam splitter 10B, a second polarization beam splitter 10C, a first polarization element 22, a first reflective SLM 32, a second polarization element 42, a second reflective SLM 52, an optical path length adjustment element 60, and a ½-wavelength plate 70.

The first and second polarization beam splitters 10B and 10C have the same configuration as the polarization beam splitter 10A of the first embodiment. That is, the first and second polarization beam splitters 10B and 10C include a light splitting surface 11 that reflects the s-polarization component of the input light and transmits the p-polarization component, a light input surface 12, a light output surface 13, a first surface 14, and a second surface 15. The first polarization beam splitter 10B receives observation light L7 including the p-polarization component and the s-polarization component using the light splitting surface 11. The observation light L7 is, for example, light of non-polarization (random polarization), circular polarization, or elliptical polarization, similarly to the first embodiment.

The first polarization element 22 is optically coupled to the second surface 15 of the polarization beam splitter 10B, and is arranged on the optical path of the first polarization component L8 reflected by the light splitting surface 11 in the observation light L7. The first polarization element 22 of this embodiment is arranged beside the light splitting surface 11 of the polarization beam splitter 10B in the X-axis direction. The first polarization element 22 has nonreciprocal optical activity for rotating the polarization plane of the first polarization component L8. Further, a definition of the nonreciprocal optical activity is the same as in the first embodiment. The first polarization element 22 preferably includes a Faraday rotator in one example.

The first reflective SLM 32 modulates the first polarization component L8 which has passed through the first polarization element 22 to generate first modulation light L9, and reflects the first modulation light L9 to the first polarization element 22. Various SLMs such as a phase modulation SLM, an intensity modulation (amplitude modulation) SLM, or a polarization modulation SLM are applied as the first reflective SLM 32, similarly to the first reflective SLM 30 of the first embodiment. The first reflective SLM 32 has a modulation surface 33 including a plurality of one-dimensionally or two-dimensionally arranged areas (pixels). The first reflective SLM 32 modulates a phase, strength or the like of the first polarization component L8 in each of the plurality of areas to generate the first modulation light L9.

The optical path length adjustment element 60 is provided on the optical path between the first polarization beam splitter 10B and the first reflective SLM 32, and adjusts an optical path length of the first polarization component L8 and the first modulation light L9. In one example, the length of the optical path length adjustment element 60 is set such that the optical path length of the first polarization component L8 and the first modulation light L9 is equal to an optical path length of a second polarization component L10 and second modulation light L11 to be described below. Although the optical path length adjustment element 60 is arranged between the first polarization beam splitter 10B and the first polarization element 22 in FIG. 4, the optical path length adjustment element 60 may be arranged between the first polarization element 22 and the first reflective SLM 32.

The first Modulation light L9 passes through the first polarization element 22 again, is transmitted through the light splitting surface 11 of the first polarization beam splitter 10B, and is output from the light output surface 13.

The second polarization beam splitter 10C is arranged beside the first polarization beam splitter 10B in the Y-axis direction so that the first surface 14 of the first polarization beam splitter 10B and the light input surface 12 of the second polarization beam splitter 10C are optically coupled to each other. The ½-wavelength plate 70 that is a polarization element having reciprocal optical activity is provided on an optical path between the first polarization beam splitter 10B and the second polarization beam splitter 10C. A polarization plane of the second polarization component L10 including a p-polarization component transmitted through the first polarization beam splitter 10B is rotated by the ½-wavelength plate 70, and is input to the light input surface 12 of the second polarization beam splitter 10C as the second polarization component L10 including the s-polarization component. The second polarization beam splitter 10C receives the second polarization component L10 including the s-polarization component using the light splitting surface 11.

The second polarization element 42 is optically coupled to the second surface 15 of the polarization beam splitter 10C and is arranged on an optical path of the second polarization component L10 reflected by the light splitting surface 11. The second polarization element 42 of this embodiment is arranged beside the light splitting surface 11 of the polarization beam splitter 10C in the X-axis direction. The second polarization element 42 has nonreciprocal optical activity for rotating the polarization plane of the second polarization component L10. Further, a definition of the nonreciprocal optical activity is the same as in the first embodiment. The second polarization element 42 preferably includes a Faraday rotator in one example.

The second reflective SLM 52 modulates the second polarization component L10 which has passed through the second polarization element 42 to generate second modulation light L11, and reflects the second modulation light L11 to the second polarization element 42. Various SLMs such as a phase modulation SLM, an intensity modulation (amplitude modulation) SLM, or a polarization modulation SLM are applied as the second reflective SLM 52, as in the second reflective SLM 50 of the first embodiment. The second reflective SLM 52 has a modulation surface 53 including a plurality of one-dimensionally or two-dimensionally arranged areas (pixels). The second reflective SLM 52 modulates a phase, strength or the like of the second polarization component L10 in each of the plurality of areas to generate second modulation light L11.

In one example, the first reflective SLM 32 and the second reflective SLM 52 are LCOS type SLMs having parallel-aligned nematic liquid crystal. The reflective SLMs 32 and 52 are not limited to an electrically addressed liquid crystal element and may be, for example, an optically addressed liquid crystal element or a deformable mirror type optical modulator. Further, when the reflective SLMs 32 and 52 are the LCOS type SLMs, only a linear polarization component of which a vibration direction is parallel to an alignment direction of the liquid crystal is modulated, and thus the reflective SLMs 32 and 52 may be arranged according to the angle of the polarization plane after rotation by the polarization elements 22 and 42.

The second modulated beam L11 passes through the second polarization element 42 again, is transmitted through the light splitting surface 11 of the second polarization beam splitter 10C, and is output from the light output surface 13.

As illustrated in FIG. 5, the observation apparatus 2C of this embodiment includes a light source 3, an illumination optical system 5A, a gathering optical system 5B, image-forming optical systems 6A and 6B, a stage 7, and photodetectors 8A and 8B, in addition to the above-described optical module 1C. Further, a configuration of the light source 3, the illumination optical system 5A, the gathering optical system 5B, and the stage 7 is the same as that in the first embodiment described above.

The image-forming optical system 6A forms an image of the first modulation light L9 output from the polarization beam splitter 10B of the optical module 1C toward the photodetector 8A. The photodetector 8A is a device that converts an input optical image into electrical image data, and is optically coupled to the light output surface 13 of the polarization beam splitter 10B via the image-forming optical system 6A. Further, the image-forming optical system 6B forms an image of the second modulation light L11 output from the polarization beam splitter 10C of the optical module 1C toward the photodetector 8B. The photodetector 8B is a device that converts an input optical image into electrical image data, and is optically coupled to the light output surface 13 of the polarization beam splitter 10C via the image-forming optical system 6B.

An operation of the optical module 1C and the observation apparatus 2C having the above configuration will be described. When the illumination light L0 is output from the light source 3, the illumination light L0 is transmitted through the observation target 4. In this case, an optical image of the observation target 4 is generated as the observation light L7. The observation light L7 passes through the gathering optical system 5B and reaches the polarization beam splitter 10B. In the observation light L7 input to the light input surface 12 of the polarization beam splitter 10B in the X-axis direction, the first polarization component L8 is reflected by the light splitting surface 11 and output from the second surface 15. Further, the second polarization component L10 is transmitted through the light splitting surface 11, and is output from the first surface 14. While the first polarization component L8 passes through the first polarization element 22, the polarization plane of the first polarization component L8 in this case is rotated, for example, 45° or 135° in a predetermined direction from the p-polarization plane by the first polarization element 22. Then, the first polarization component L8 is modulated by the first reflective SLM 32 to be the first modulation light L9 and is simultaneously reflected to the first polarization element 22. The first modulation light L9 passes through the first polarization element 22 again, but in this case, the polarization plane of the first modulation light L9 is rotated, for example, 45° or 135° in the above predetermined direction by the first polarization element 22. As a result, the first modulation light L9 mainly includes the p-polarization component (or consists of only the p-polarization component).

Then, the first modulation light L9 including the p-polarization component is transmitted through the light splitting surface 11 of the polarization beam splitter 10B, and is output from the light output surface 13 of the polarization beam splitter 10B. An image is formed from the first modulation light L9 by the image-forming optical system 6A and imaged by the photodetector 8A.

On the other hand, the second polarization component L10 including a p-polarization component is transmitted through the light splitting surface 11 of the polarization beam splitter 10B, passes through the ½-wavelength plate 70, and reaches the light splitting surface 11 of the polarization beam splitter 10C. When the second polarization component L10 passes through the ½-wavelength plate 70, the polarization plane of the second polarization component L10 is rotated, for example, 90° in a certain rotation direction from the p-polarization plane. Therefore, the second polarization component L10 mainly includes the s-polarization component (or consists of only the s-polarization component), and is reflected by the light splitting surface 11 of the polarization beam splitter 10C.

Also, while the second polarization component L10 passes through the second polarization element 42, the polarization plane of the second polarization component L10 in this case is rotated, for example, 45° or 135° in a predetermined direction from the s-polarization plane by the second polarization element 42. Then, the second polarization component L10 is modulated by the second reflective SLM 52 to be the second modulation light L11 and is simultaneously reflected to the second polarization element 42. The second modulation light L11 passes through the second polarization element 42 again, but in this case, the polarization plane of the second modulation light L11 is rotated, for example, 45° or 135° in the above predetermined direction by the second polarization element 42. As a result, the second modulation light L11 mainly includes the p-polarization component (or consists of only the p-polarization component).

Then, the second modulation light L11 including the p-polarization component is transmitted through the light splitting surface 11 of the polarization beam splitter 10C, and is output from the light output surface 13 of the polarization beam splitter 10C. An image is formed from the second modulation light L11 by the image-forming optical system 6B and imaged by the photodetector 8B.

According to the optical module 1C and the observation apparatus 2C of the present embodiment described above, it is possible to obtain the same effects as those of the optical module 1A and the observation apparatus 2A of the first embodiment described above. That is, in the present embodiment, the p-polarization component (first polarization component L8) of the observation light L7 and the s-polarization component (second polarization component L10) can be separated and then modulated, and the first and second modulation lights L9 and L11 after modulation can be individually output. Therefore, according to the optical module 1C and the observation apparatus 2C of the present embodiment, it is possible to effectively use both of the p-polarization component and the s-polarization component of the observation light L7 and increase light use efficiency. Thus, it is possible to observe the observation light. L7 with a larger amount of light than in a conventional case, and to clearly observe the observation target 4 even when light intensity of the observation light L7 is very small.

Further, according to the optical module 1C and the observation apparatus 2C of the present embodiment, different modulation patterns can be applied to the first and second modulation lights L9 and L11. Accordingly, for example, two modulation patterns having a different optical phase distribution or light intensity distribution within a plane perpendicular to the optical axis can be applied. Alternatively, it is possible to correct the aberrations independently for each polarization component. Thus, according to the optical module 1C and the observation apparatus 2C of the present embodiment, it is possible to provide a user with a variety of observation forms, as compared to a conventional device. Further, in the present embodiment, the first reflective SLM 32 and the second reflective SLM 52 may present the same modulation pattern.

Further, according to the optical module 1C, the light can be input and reflected in normal directions of the respective modulation surfaces 33 and 53 of the reflective SLMs 32 and 52, and thus it is easy to adjust the optical axis and it is possible to increase efficiency of input to the SLM and efficiency of output from the SLM. Further, the optical axis of the observation light L7 and each of the optical axes of the first and second modulation lights L9 and L11 can be caused to be orthogonal rather than oblique, and thus it is possible to facilitate a connection to the gathering optical system 5B or the image-forming optical system 6A or 6B and to reduce generation of aberrations. Further, since the light is caused to reciprocate in a part of the optical path, it is possible to simplify and miniaturize the configuration of the entire optical system.

Further, as in this embodiment, it is preferable that the polarization element (for example, the ½-wavelength plate 70) having reciprocal optical activity be provided on the optical path between the first polarization beam splitter 10B and the second polarization beam splitter 10C. Accordingly, the polarization plane of the second polarization component L10 including the p-polarization component transmitted through the light splitting surface 11 of the first polarization beam splitter 10B can be rotated to include the s-polarization component, and the second polarization component L10 can preferably be reflected by the light splitting surface 11 of the second polarization beam splitter 10C. Further, accordingly, the light distribution direction of the liquid crystal of the first reflective SLM 32 and the light distribution direction of the liquid crystal of the second reflective SLM 52 can be aligned (parallelized to each other), and control of the first and second reflective SLMs 30 and 50 can be common to modulation data input to the first and second reflective SLMs 32 and 52.

Third Embodiment

Figure 6:
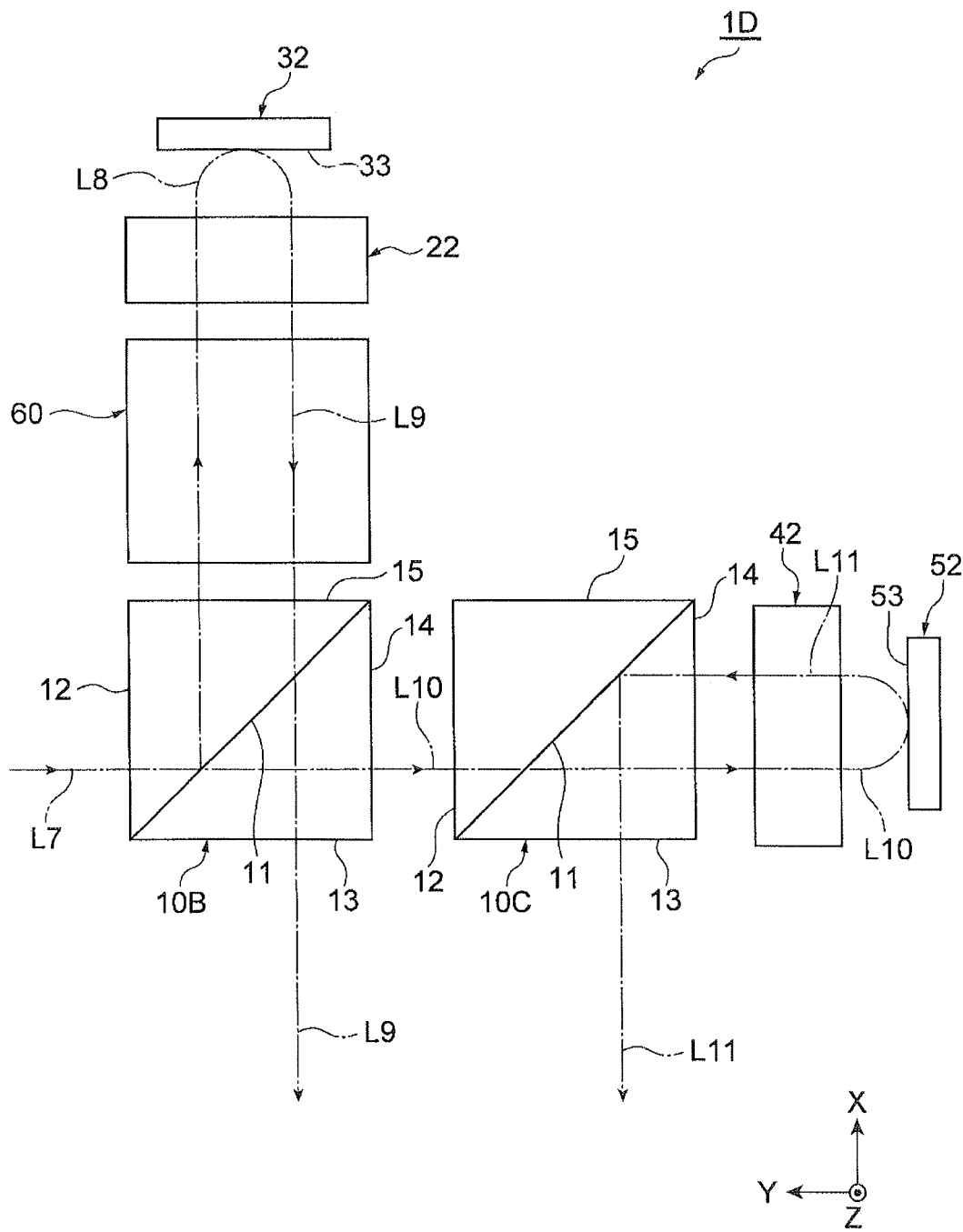
FIG. 6 is a diagram illustrating a configuration of an optical module according to a third embodiment of the present invention.
Figure 7:
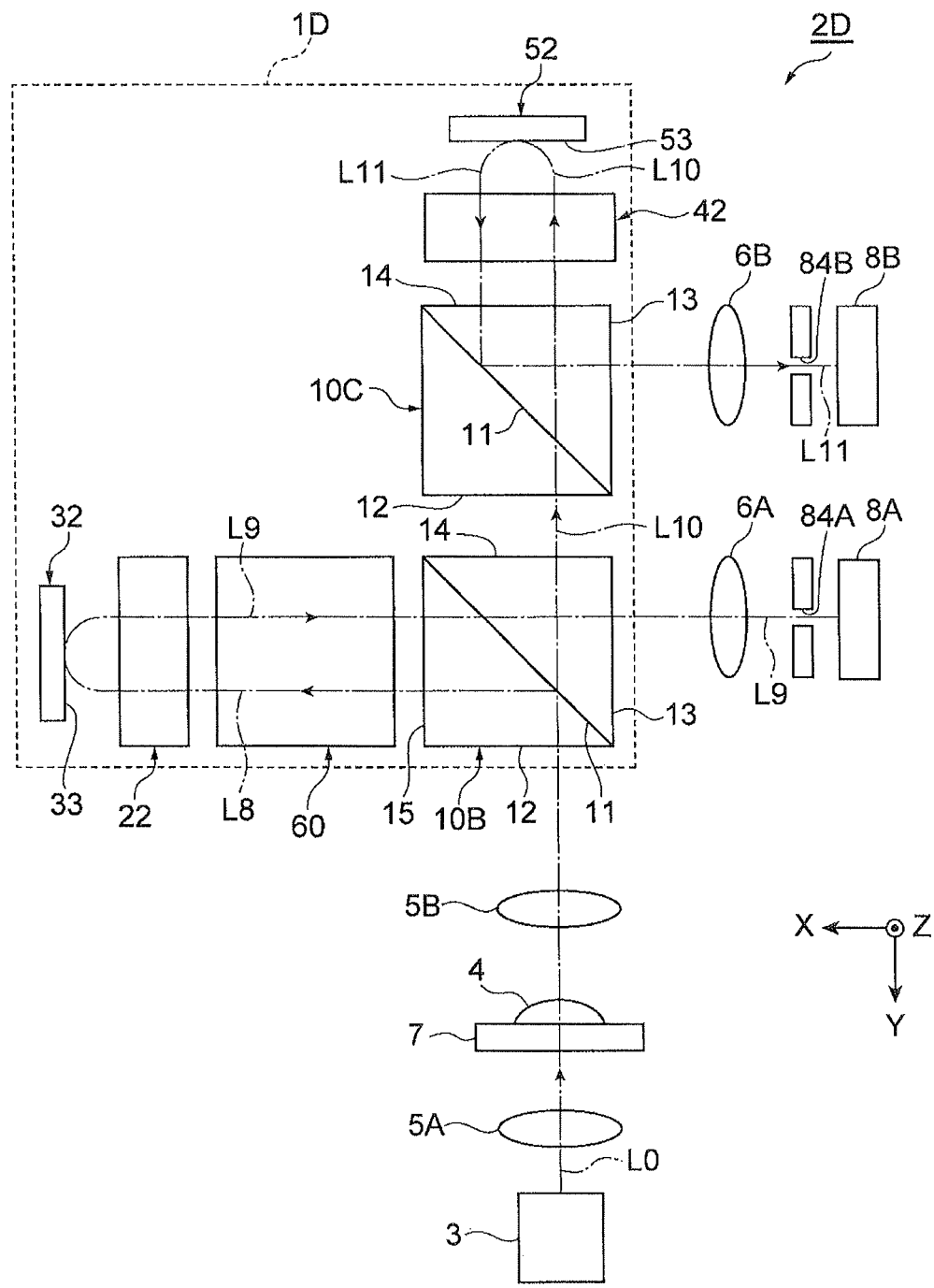
FIG. 7 is a diagram illustrating a configuration of an observation apparatus including the optical module of the third embodiment.

FIG. 6 is a diagram illustrating a configuration of an optical module 1D according to a third embodiment of the present invention. Further, FIG. 7 is a diagram illustrating a configuration of an observation apparatus 2D including the optical module 1D. The optical module 1D of this embodiment is different from the optical module 1C of the second embodiment in an arrangement of the second polarization element 42 and the second reflective SLM 52 and omission of the ½-wavelength plate 70. Further, the observation apparatus 2D of the present embodiment includes pinholes 84A and 84B.

In this embodiment, the second polarization element 42 is optically coupled to a first surface 14 of the second polarization beam splitter 10C, and is arranged on an optical path of the second polarization component L10 transmitted through the light splitting surface 11 of the second polarization beam splitter 10C. The second polarization element 42 of this embodiment is arranged beside the light splitting surface 11 of the polarization beam splitter 10C in the Y-axis direction. The second reflective SLM 52 modulates the second polarization component L10 which has passed through the second polarization element 42 to generate second modulation light L11, and reflects the second modulation light L11 to the second polarization element 42.

In the above configuration, the second polarization component L10 including the p-polarization component transmitted through the light splitting surface 11 of the second polarization beam splitter 10C passes through the second polarization element 42. In this case, the polarization plane of the second polarization component L10 is rotated, for example, 45° in a predetermined direction from a p-polarization plane by the second polarization element 42. Then, the second polarization component L10 is modulated by the second reflective SLM 52 to be second modulation light L11, and is simultaneously reflected to the second polarization element 42. While the second modulation light L11 passes through the second polarization element 42 again, the polarization plane of the second modulation light L11 in this case is rotated, for example, 45° in the above predetermined direction by the second polarization element 42. As a result, the second modulation light L11 mainly includes an s-polarization component (or consists of only the s-polarization component). Then, the second modulation light L11 including the s-polarization component is reflected by the light splitting surface 11 of the second polarization beam splitter 10C, and output from the light output surface 13 of the second polarization beam splitter 10C.

The pinhole 84A is arranged on the optical path between the image-forming optical system 6A and the photodetector 8A, and the first modulation light L9 of which the image has been formed by the image-forming optical system 6A passes through the pinhole 84A and reaches the photodetector 8A. Further, the pinhole 84B is arranged on the optical path between the image-forming optical system 6B and the photodetector 8B, and the second modulation light L11 of which the image has been formed by the image-forming optical system 6B passes through the pinhole 84B and reaches the photodetector 8B. Since the pinholes 84A and 84B are provided, it is possible to reduce noise light included in the first and second modulation lights L9 and L11 of which the image has been formed by the image-forming optical systems 6A and 6B, and enable clearer observation.

According to the optical module 1D and the observation apparatus 2D of the present embodiment, it is possible to effectively use both the p-polarization component and the s-polarization component of the observation light L7 and to increase light use efficiency, similarly to the second embodiment. Further, since different modulation patterns are applied to the first and second modulation lights L9 and L11, it is possible to provide the user with a wider variety of observation forms than in a conventional device. Further, since the light can be input and reflected in a normal direction of the respective modulation surfaces 33 and 53 of the reflective SLMs 32 and 52, it is possible to facilitate a connection to the gathering optical system 5B or the image-forming optical systems 6A and 6B, and miniaturize the entire optical system.

Fourth Embodiment

Figure 8:
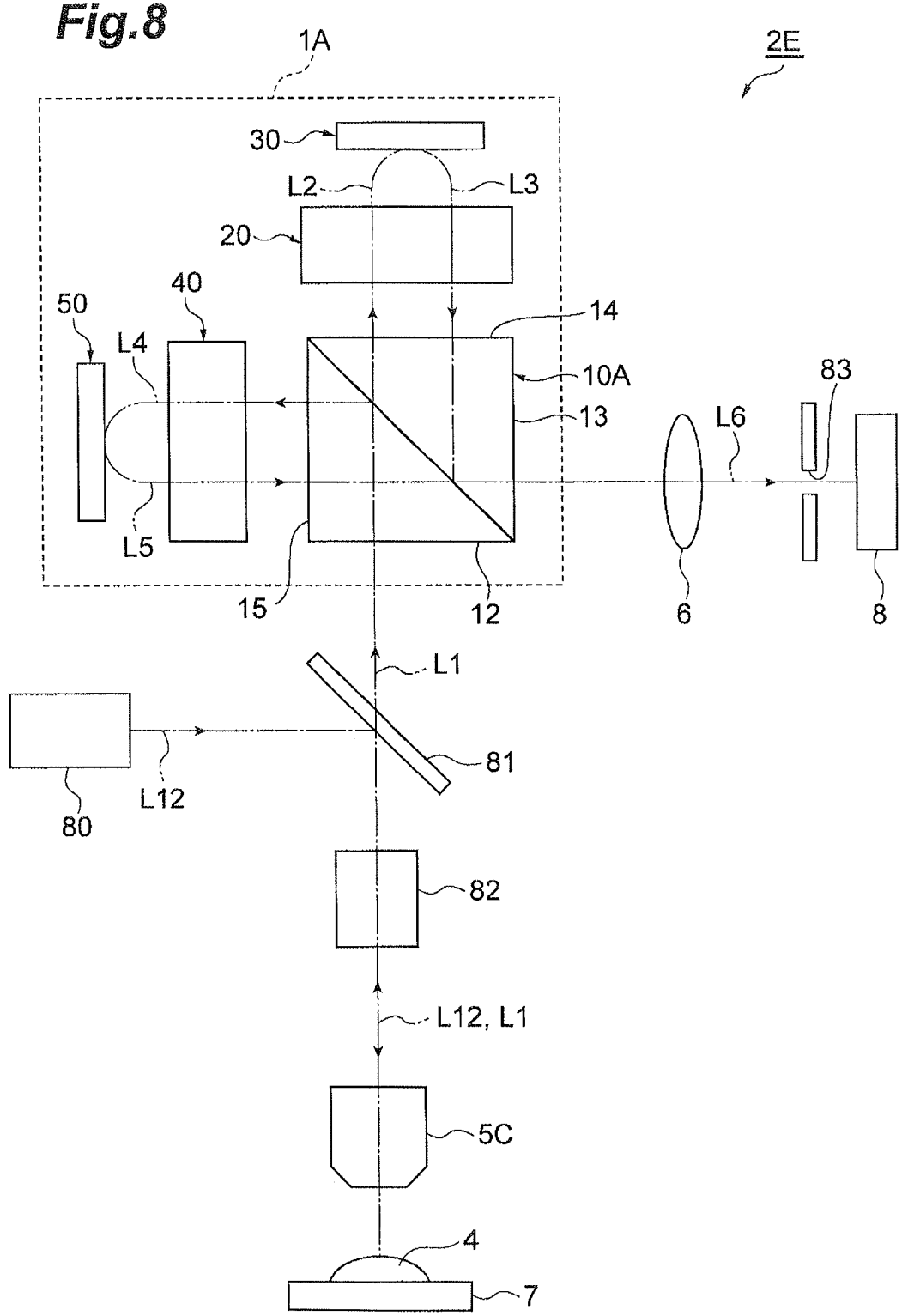
FIG. 8 is a diagram illustrating a configuration of a confocal fluorescence microscope as an observation apparatus according to a fourth embodiment of the present invention.

FIG. 8 is a diagram illustrating a configuration of a confocal fluorescence microscope 2E as an observation apparatus according to a fourth embodiment of the present invention. This confocal fluorescence microscope 2E is different from the observation apparatus 2A of the first embodiment in a scheme of irradiating an observation target 4 with irradiation light, and inclusion of a pin hole 83.

The confocal fluorescence microscope 2E includes a light source 80, a dichroic mirror 81, and a beam scanner 82, and an objective lens 5C, in place of the light source 3, the illumination optical system 5A, and the gathering optical system 5B of the first embodiment. The light source 80 outputs excitation light L12 (non-polarization light in one example) including a p-polarization component and an s-polarization component. The dichroic mirror 81 is arranged on an optical path connecting a light input surface 12 of a polarization beam splitter 10A to an observation target 4, reflects the excitation light L12 from the light source 80 to the observation target 4, and transmits observation light (fluorescence) L1 from the observation target 4 toward the polarization beam splitter 10A. The objective lens 5C is arranged on an optical path between the observation target 4 and the dichroic mirror 81, gathers the excitation light L12 on the observation target 4, and guides the observation light (fluorescence) L1 generated from the observation target 4 toward the polarization beam splitter 10A. The beam scanner 82 can move a gathering position of the excitation light L12 in the observation target 4 in a plane perpendicular to an optical axis, and performs scanning of the excitation light L12 with respect to the observation target 4. A fluorescence image is obtained by the beam scanner 82 scanning the excitation light L12 two-dimensionally or three-dimensionally. Further, a relay lens may be inserted between the beam scanner 82 and the objective lens 5C. Further, a relay lens may be inserted between the beam scanner 82 and the optical module 1A.

Further, a pinhole 83 is arranged on an optical path between an image-forming optical system 6 and a photodetector 8, and combined modulation light L6 of which an image has been formed by the image-forming optical system 6 passes through the pinhole 83 and reaches the photodetector 8. Since the pin hole 83 is provided, it is possible to reduce noise light included in the combined modulation light L6 of which the image has been formed by the image-forming optical system 6, and enable clearer observation.

According to the confocal fluorescence microscope 2E of this embodiment, it is possible to effectively use both the p-polarization component and the s-polarization component of the observation light (fluorescence) L1 and increase light use efficiency, and thus it is possible to perform clear fluorescence observation even when light intensity of the observation light (fluorescence) L1 is very small, similarly to the observation apparatus 2A of the first embodiment. Further, since different modulation patterns can be applied to the first and second modulation lights L3 and L5, it is possible to provide the user with a wider variety of observation forms than in a conventional confocal fluorescence microscope. Further, since the light can be input and reflected in a normal direction of the modulation surfaces 31 and 51 of the reflective SLMs 30 and 50, it is possible to facilitate a connection of an optical system such as the dichroic mirror 81, the objective lens 5C, or the image-forming optical system 6, and to miniaturize the entire optical system.

Further, while the confocal fluorescence microscope including the optical module 1A of the first embodiment has been described in the present embodiment, the confocal fluorescence microscope may include the optical module 1B of the first modification example, the optical module 1C of the second embodiment, or the Optical module 1D of the third embodiment. By including one of the optical modules, it is possible to preferably achieve the above-described effects. Further, while the light source 80 and the dichroic mirror 81 are installed between the optical module 1A and the beam scanner 82 in FIG. 8, the light source 80 and the dichroic mirror 81 may be installed between the image-forming lens 6 and the optical module 1A.

The optical module and the light irradiation device according to the present invention are not limited to the above-described embodiments, and various other modifications are possible. For example, while the example in which the optical module of the present invention has been applied to the confocal fluorescence microscope is shown in the fourth embodiment, the optical module of the present invention may be applied to microscopic observation, eyeground observation, a laser scanning microscope that is not confocal, a microscope using a camera, a transmission microscope, or the like. Further, the optical module of the present invention may be applied to a non-fluorescence observation microscope, such as a back-scattered light observation microscope or various Raman scattering observation microscopes.

Further, while the polarization beam splitter having a rectangular section is used in each of the above embodiments, a shape of the polarization beam splitter is not limited thereto, and may be, for example, a plate shape. Further, while the light is input and output vertically with respect to the reflective SLM in each of the above embodiments, input and reflection angles with respect to the reflective SLM may be greater than 0°.

Further, aberrations are generally generated in an optical system including the SLM. However, in each of the above embodiments, a pattern for correcting the aberrations may be indicated in the first and second reflective SLMs. By applying such a pattern to a desired phase pattern, it is possible to correct the aberrations. In this case, aberrations generated in the first modulation light and aberrations generated in the second modulation light may be independently obtained and individually removed in the first and second reflective SLMs.

Further, while the observation target is illuminated in a transmission manner and the transmitted light becomes the observation light in the first to third embodiments, reflected light or scattered light from the observation target that is dark-field illuminated may be the observation light. Fluorescent Raman scattered light, parametric oscillation light, or harmonic light generated by illuminating the observation target may be the observation light.

INDUSTRIAL APPLICABILITY

The present invention can be applied as use of the optical module and the observation apparatus capable of increasing light use efficiency.

REFERENCE SIGNS LIST 1A to 1D: optical module, 2A, 2C, and 2D: observation apparatus, 2E: confocal fluorescence microscope, 3: light source, 4: observation target, 5A: illumination optical system, 5B: gathering optical system, 5C: objective lens, 6, 6A, and 6B: image-forming optical system, 7: stage, 8, 8A, and 8B: photodetector, 10A: polarization beam splitter, 10B: first polarization beam splitter, 10C: second polarization beam splitter, 11: light splitting surface, 12: light input surface, 13: light output surface, 14: first surface 15: second surface, 20 and 22: first polarization element, 30 and 32: first reflective SLM, 31 and 33: modulation surface, 50 and 52: second reflective SLM, 40 and 42: second polarization element, 50 and 52: second reflective SLM, 51 and 53: modulation surface, 60: optical path length adjustment element, 70: ½-wavelength plate, 80: light source, 81: dichroic mirror, 82: beam scanner, 83, 84A, and 84B: pinhole, 90: ½-wavelength plate, L0: illumination light, L1 and L7: observation light, L2 and L8: first polarization component, L3 and L9: first modulation light, L4 and L10: second polarization component, L5 and L11: second modulation light, L6: combined modulation light, L11: second modulation light, L12: excitation light.

The invention claimed is:

1. An optical module comprising:
a polarization beam splitter including a light splitting surface configured to reflect an s-polarization component included in input light and transmit a p-polarization component;
a first polarization element including a Faraday rotator arranged on an optical path of a first polarization component in the input light transmitted through the light splitting surface and configured to rotate a polarization plane of the first polarization component;
a first reflective spatial light modulator configured to modulate the first polarization component passing through the first polarization element to generate first modulation light, and reflect the first modulation light to the first polarization element;
a second polarization element including a Faraday rotator arranged on an optical path of a second polarization component in the input light reflected by the light splitting surface and configured to rotate a polarization plane of the second polarization component; and
a second reflective spatial light modulator configured to modulate the second polarization component passing through the second polarization element to generate second modulation light, and reflect the second modulation light to the second polarization element,
wherein the first modulation light passing through the first polarization element and then reflected by the light splitting surface and the second modulation light passing through the second polarization element and then transmitted through the light splitting surface are combined with each other and output from the polarization beam splitter,
wherein the polarization plane of the first polarization component before modulation may be rotated 45° by the first polarization element, and a polarization plane of the first modulation light after modulation may be further rotated 45° by the first polarization element, and
wherein the polarization plane of the second polarization component before modulation may be rotated 45° by the second polarization element, and a polarization plane of the second modulation light after modulation may be further rotated 45° by the second polarization element.

2. The optical module according to claim 1, wherein the first and second reflective spatial light modulators are liquid crystal types, and
an alignment direction of liquid crystal of the first reflective spatial light modulator and an alignment direction of liquid crystal of the second reflective spatial light modulator are orthogonal to each other.

3. The optical module according to claim 1, further comprising:
a polarization element arranged on an optical path between the polarization beam splitter and the first reflective spatial light modulator or on an optical path between the polarization beam splitter and the second reflective spatial light modulator,
wherein the polarization element is either the first polarization element or the second polarization element.

4. An observation apparatus, comprising:
the optical module according to claim 1;
a gathering optical system configured to gather an observation light from the observation target and cause the observation light to be input as the input light to the optical module;
an image-forming optical system configured to form an image of light output from the optical module; and
a photodetector configured to detect light from which the image has been formed by the image-forming optical system.

5. The observation apparatus according to claim 4, further comprising:

a pinhole arranged on an optical path between the image-forming optical system and the photodetector.

* * * * *